United States Patent [19]

Altnether et al.

[11] Patent Number: 4,625,723

[45] Date of Patent: Dec. 2, 1986

[54] PENCIL FOR ELECTROSURGICAL GENERATOR

[75] Inventors: Paul J. Altnether, Largo; Frederick W. Rexroth, Dunedin, both of Fla.

[73] Assignee: Medical Research Associates, Ltd. #1, Clearwater, Fla.

[21] Appl. No.: 705,966

[22] Filed: Feb. 26, 1985

[51] Int. Cl.⁴ ............................................. A61B 17/36
[52] U.S. Cl. ............................ 128/303.1; 128/303.14; 128/303.17
[58] Field of Search .......... 128/303.1, 303.13, 303.14, 128/303.15, 303.16, 303.17, 303.18, 303.19, 800, 801; 200/157, 302.2, 159, 340, DIG. 25

[56] References Cited

U.S. PATENT DOCUMENTS

| | | | |
|---|---|---|---|
| 3,932,722 | 1/1976 | Obata et al. | 200/302.2 |
| 4,032,738 | 6/1977 | Esty et al. | 128/303.13 |
| 4,046,975 | 10/1977 | Seeger, Jr. | 200/302.2 |
| 4,545,375 | 10/1955 | Cline | 128/303.17 |

Primary Examiner—Kyle L. Howell
Assistant Examiner—Randy Citrin
Attorney, Agent, or Firm—Epstein & Edell

[57] ABSTRACT

A pencil for electrosurgical generators includes a push button switch structure useful in selectively bridging spaced printed circuit contacts in spite of oxidized film on the contact surface. A movable concave disk has a sharp peripheral edge that is forced against the contact surface during switch actuation to cut through the oxidized film and reliably bridge the contacts. The disk is carried by an axial projection forming part of a resilient dome surrounding the projection. The dome includes a radial flange which is compressed against the printed circuit board by an annular member projecting axially inwardly from the housing wall around the outside of the dome. The closed end of the dome is connected to the flange by a frusto-conical connecting wall adapted to flex to permit the closed dome end to be pushed toward the open dome end during switch actuation.

16 Claims, 7 Drawing Figures

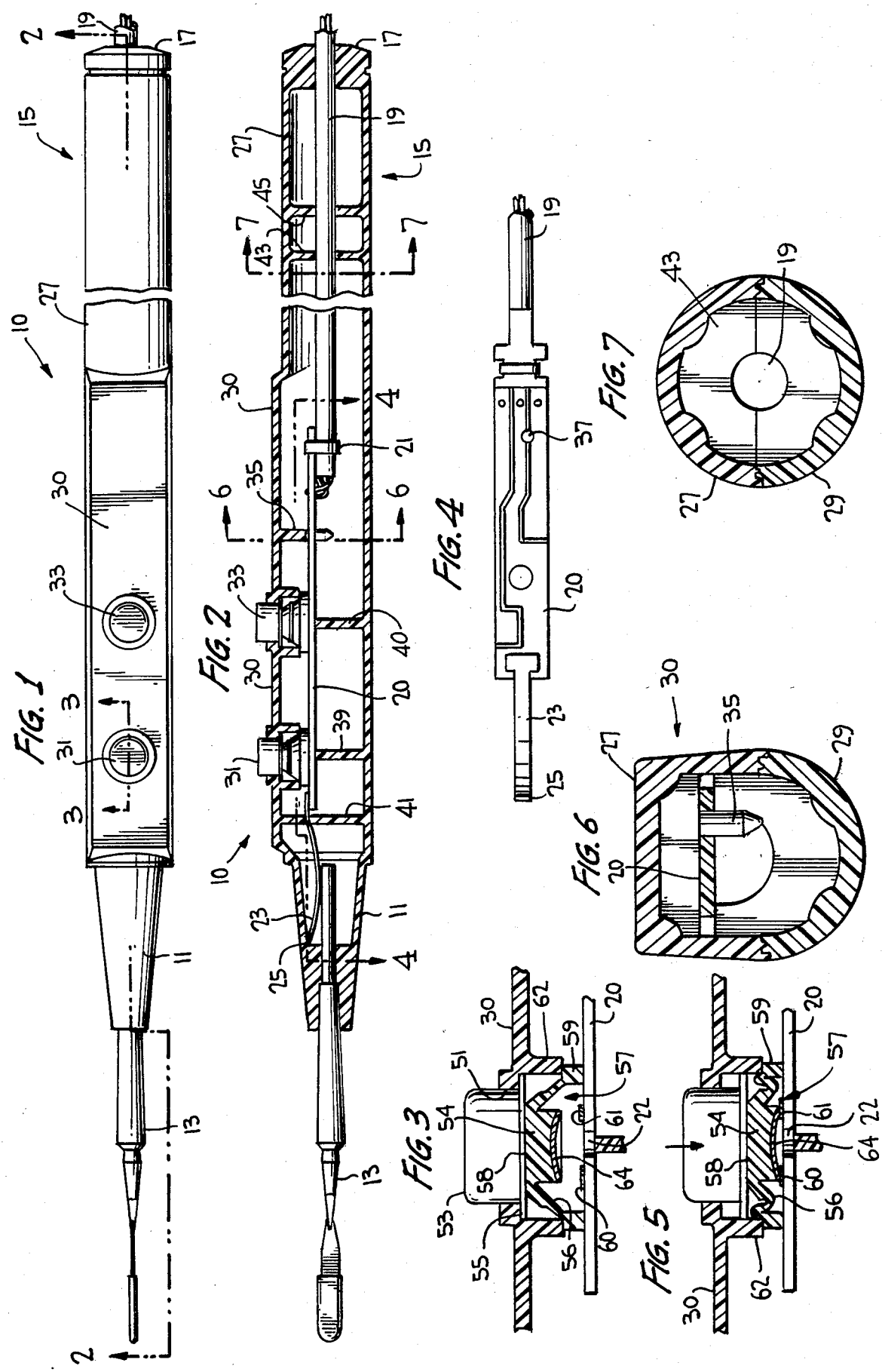

PENCIL FOR ELECTROSURGICAL GENERATOR

BACKGROUND OF THE INVENTION

1. Technical Field

The present invention relates to electrosurgical pencils and, more particularly, to electrosurgical pencils carrying electrical switches for controlling application of command signals to electrosurgical generators.

2. Discussion of the Prior Art

Electrosurgical techniques have become widely used by surgeons in recent years. Accordingly, a need has developed for equipment that is easy to handle and operate, reliable and safe. Electrosurgical equipment normally includes a generator providing high frequency electrical cutting and coagulation signals for application to an electrode mounted in a handle, the latter electrode and handle combination being referred to herein as a pencil. The pencil is preferably long and slender so as to be held by the surgeon during surgery in the manner of a writing implement. In order to permit the surgeon to control the high frequency signals supplied to the electrode (for example, a continuous a.c. signal for cutting, or a pulse a.c. signal for coagulation), switches are mounted on the pencil and are selectively actuable to control application of command signals to the electrosurgical generator. In this manner, the switches permit selective generation of the cut and coagulation signals. The switches, of course, must be sealed to prevent intrusion of fluids and other contaminants into the pencil interior, and must be completely reliable to assure proper operation of concomitant precision and safety.

While there have been many attempts to produce electrosurgical pencils with finger-operated switches, there remains room for considerable improvement to increase durability and to assure proper and reliable switching operation at all times during use of the pencil. It is to this purpose that the present invention is directed.

Examples of prior art electrosurgical pencils are described and illustrated in the following U.S. patents: U.S. Pat. Nos. 3,911,241 (Garrard); 4,021,630 (Taylor); 4,032,738 (Esty et al); 4,034,761 (Prater et al); 4,112,950 (Pike); 4,170,234 (Graham); and 4,289,943 (Sadao).

The Taylor patent discloses a resilient contact switch formed of a flexible cap having an arcuate dome and a cylindrical upstanding sidewall. The sidewall is positioned to be sealed within a sleeve in the pencil housing by virtue of the cap being larger than the sleeve bore, thereby resulting in radial compression of the sidewall. A plunger extends inwardly from the dome to permit selective deflection of a concave metal plate at the distal end of the plunger to establish a connection contact between contacts on a circuit board. In a second embodiment disclosed in the Taylor patent, a conductive material can be used for the plunger, or a conductive plate may be bonded to the lower surface of the plunger.

The Esty et al patent discloses a generally flat electrosurgical pencil providing electrical interface between an electrosurgical signal generator and an exposed surgical electrode. Esty et al expressly state that the resilient contact switch of the Taylor patent could be used with the Esty et al pencil. The flat, elongated configuration of the housing of the Esty et al pencil is designed to approximate the flat handle feel of previous passive surgical instruments. A bore extending through one of the flat rigid surfaces comprising the pencil housing is outwardly encircled by an upright cylindrical wall terminating in inwardly turned shoulders. A momentary switch assembly includes a hollow peripheral sidewall retained in sealing engagement internal to the housing bore and the upright cylinder wall, and a cap having a cross section which is outwardly arcuate. Important aspects of the Esty et al pencil are the flexible cap with cylindrical sidewalls retained in sealed abutting engagement within the collar of the housing opening, and a closure extending across the sidewalls and having an external arcuate cross section.

The sidewall sealing arrangement required for the switch disclosed in both the Taylor and Esty et al patents is effective for sealing; however, the switch presents problems during fabrication. Specifically, the outside diameter of the sidewalls of the resilient member and the inside diameter of the receiving bore must be such that a tight seal is effected; however, if the fit between the two is too tight, it becomes extremely difficult to insert the resilient member into the bore during assembly of the unit.

In addition to the foregoing, prior art electrosurgical pencil switches, when used in conjunction with printed circuit boards, tend to be unreliable. Specifically, an oxidized film inherently forms on all metallic switch contacts on printed circuit boards. When a movable metallic surface is used to selectively bridge such contacts, the oxidized film often prevents good electrical connection between the movable surface and the circuit board contacts, thereby preventing the desired circuit closure.

OBJECTS AND SUMMARY OF THE INVENTION

Accordingly, it is an object of the present invention to provide a reliable, safe and easily operable electrosurgical pencil having an improved control switch configuration that greatly facilitates the pencil assembly process without sacrificing the effectiveness of the seal required between the pencil interior and the external environment.

Another object of the present invention is to provide an improved electrosurgical pencil having a control switch capable of reliable operation in conjunction with printed circuits in spite of oxidixing film that may form on the printed circuit contacts.

It is a further object of the present invention to provide a functionally reliable and easily fabricated control switch as part of an improved electrosurgical generator pencil.

Still another object of the present invention is to provide an improved contact member for selectively bridging two stationary printed circuit contacts in an electrosurgical pencil.

In accordance with the present invention an electrosurgical pencil includes a switch structure to effect an environmental seal along one or more pairs of abutting surfaces disposed substantially perpendicular to switch actuation direction, rather than along surfaces extending parallel to or concentrically about the switch actuation direction. The need for precisely fitting a resilient member into a bore in sealing relation is thereby eliminated. This desirable result is achieved by a resilient dome-like member including a flange extending radially outward in a plane perpendicular to the switch actuation direction and which is compressed against a circuit board by an annular projection surrounding the dome and the switch access opening in the housing. The closed dome end is joined to the flange by a generally frusto-conical wall which flexes along its length to permit the closed end of the member to be axially displaced toward the circuit board when the switch is actuated. An axial projection portion of the dome-like member extends within the member interior and terminates in a concave surface spaced from the circuit board. A concave metal disk, conforming to the concave distal end of the axial projection, includes a sharp circumferential edge which contacts the circuit board at two stationary switch contacts when the switch is actuated. The sharp edge cuts through any oxidized film which may be formed on the stationary contacts to assure proper electrical connection between those contacts by the bridging disk.

BRIEF DESCRIPTION OF THE DRAWINGS

These and other objects, features and many of the attendant advantages of the invention will be better understood upon a reading of the following detailed description considered in conjunction with the accompanying drawings wherein like parts in each of the several figures are identified by the same reference numerals, and wherein:

FIG. 1 is a top view in plan of an electrosurgical generator pencil constructed in accordance with the present invention;

FIG. 2 is a view in section taken along lines 2—2 of FIG. 1;

FIG. 3 is a view in section taken along lines 3—3 of FIG. 1 and showing a switch structure of the present invention in its unactuated position;

FIG. 4 is a top view in plan taken along lines 4—4 of FIG. 2 and showing a printed circuit board utilized as part of the electrosurgical generator pencil;

FIG. 5 is a view in section similar to the view in FIG. 3 but showing the switch in its actuated position;

FIG. 6 is a view in section taken lines 6—6 of FIG. 2; and

FIG. 7 is a view in section taken along lines 7—7 of FIG. 2.

DESCRIPTION OF THE PREFERRED EMBODIMENTS

Referring to the drawings in greater detail, a pencil for an electrosurgical generator includes an elongated hollow housing 10 having a tapered forward end 11 from which a blade-electrode unit 13 projects through a suitably defined bore. The rearward section 15 of the housing is generally cylindrical and terminates in a rear end wall 17 from which a cable assembly 19 extends through a suitably provided aperture. The cable assembly 19 extends through the hollow housing interior to one end of a printed circuit board 20 to which the cable assembly is tied by wire tie 21. Wires in the cable assembly 19 are electrically connected to the appropriate circuit points on the underside of the printed circuit board. An electrode contact 23 for the electrosurgical cutting/coagulation signal is secured to the other end of printed circuit board 20 and extends forwardly therefrom into biased electrical contact with the blade-electrode unit 13. More specifically, electrode contact 23 is a resilient strip of electrically conductive metal or alloy, such as brass, which is bowed so as to be forced against the blade-electrode 13 by virtue of the distal end 25 of the contact 23 being restrained against the inner surface of the housing wall inside tapered housing section 11.

Housing 10 is preferably formed from two elongated housing parts 27 and 29 which are substantially identical in outer configuration except for a longitudinally intermediate handle section 30 of the housing. At section 30, housing part 27 has an open rectangular, rather than semi-cylindrical, cross section and houses two control switches 31 and 33. Switches 31 and 33 are positioned to interact with different longitudinally spaced circuit locations on the circuit side of printed circuit board 20, and serve to provide control signals to an electrosurgical generator via cable assembly 19. The control signals, in turn, control the application and nature of the high frequency cutting/coagulation signals applied to the blade-electrode 13.

A locating pin 35 is formed integrally with housing part 27 and extends from the inner surface of that housing part, in section 30, to the housing interior. Locating pin 35 mates with a locating aperture 37 in printed circuit board 20 to permit proper longitudinal positioning of the printed circuit boad during assembly of the pencil. Two semicircular support elements 39, 40 are provide integrally with housing part 29 and have respective support edges for fixing the transverse position of the printed circuit board relative to the housing walls. Specifically, elements 39 and 40 determine the precise spacing between the circuit surface of printed circuit board 20 and the switches 31 and 33.

The housing 10 is formed by ultrasonic welding to join the two housing parts 27 and 29 once the printed circuit board 20, cable assembly 19 and blade-electrode unit 13 are properly positioned. A water tight seal 41 is formed about the contact 23 to seal off the forward part of the housing interior (i.e., containing the rearward end of the blade-electrode unit 13) from the portion of the housing interior which contains the printed circuit board 20. Water tight seal 41 is formed by melting an energy director during the ultrasonic welding process. Two additional water tight seals 43 and 45 are formed about the cable assembly in housing section 15 during the ultrasonic welding process. Water tight seals 43 and 45 are generally circular molded parts of their respective housing elements, apertured to receive and crimp the cable assembly to provide a water tight fit along with strain relief for the cable assembly.

The two switches 31 and 33 are substantially identical in structure and only switch 31 is illustrated in detail in FIGS. 3 and 5 to which specific reference is now made. An access aperture 51 defined in housing part 27 in section 30 is positioned over contact regions on circuit board 20 to be bridged by the switch. A push button actuator 53 has a radially-extending flange 55 at one end to mate with a shoulder in the housing wall and retain the push button in access aperture 51. Flange 55 is biased against the housing shoulder by means of a resilient dome-shaped member 57. The dome-shaped member 57 tapers from its lower open end, defined as an annular flange 59, to a closed circular end 58 having a flat circular configuration. End 58, when the switch is unactuated, abuts the bottom surface of push button 53 and biases flange 55 against the retaining shoulder surrounding access aperture 51. Flange 59 of the resilient member 57 has its lower surface disposed in flush sealing contact with the circuit-defining top surface of printed circuit board 20, surrounding two spaced and mutually isolated contact portions 60, 61 on the circuit board. The upper exposed annular surface of flange 59 sealingly abuts an annular structural member 62 formed integrally with housing section 30. Member 62 surrounds access aperture 51 and projects generally toward printed circuit board 20. Flange 59 thus provides fluid pressure seals at both of its oppositely facing upper and lower surfaces.

A vent hole 22 is defined in printed circuit board 20 under dome-shaped member 57 to permit air from the housing interior to enter and leave the interior space beneath member 57 when the switch is actuated and de-actuated.

Resilient member 57 includes a peripherally continuous connecting wall 56 formed integral with and connecting the closed circular end 58 and flange 59. Connecting wall 56 tapers in a generally frusto-conical configuration and is flexible to permit closed end 58 to be pushed axially toward the printed circuit board 20. Flexibility in connecting wall 56 is enhanced by providing two thickness sections thereof; that is, the smaller diameter portion of the wall, extending from closed end 58, is approximately twice as thick as the larger diameter portion extending from flange 59. As best illustrated in FIG. 5, wall 56 flexes at the juncture between the two wall thicknesses to provide a reliable and repeatable flexure location assuring proper switch actuation.

A generally cylindrical axial projection member 54 extends from closed end 58 into the dome interior space and towards printed circuit board 20. Projection member 54 is approximately axially co-extensive with connecting wall 56 so that the distal end of the projecting member is spaced from the printed circuit board in the unflexed, unactuated position of the dome member as represented in FIG. 3. The concave distal end of projection member 54 is fitted with a similarly concave metal contact disc 64. The exposed annular peripheral edge of disc 64 is sufficiently sharp to permit the edge to cut through any oxide film which may form on contacts 60, 61. In this regard, the annular edge of disc 64 is positioned above contacts 60, 61 so that when push button 53 is depressed, disc 64 bridges contacts 60 and 61 with an electrically conductive path. Disc 64 is substantially the same size and shape as the concave distal end of resilient projection 54 and is collapsible therewith so that the sharp circumferential edge expands diametrically if forced against contacts 60, 61 after the original actuation contact is made. This expansion causes the sharp edge of the disc to further scrape the surfaces of contacts 60, 61 to assure positive and reliable electrical contact, even through the aforesaid oxide film.

The water-tight seals 41, 43, 45, formed by melting of respective energy directors during ultrasonic welding of the housing parts, are used to prevent liquid from being introduced into the compartment housing printed circuit board 20. The dome members 57 provide further sealing, in this regard, at the switches, particularly by virtue of flange 59 being compressed between annular projection 62 and the printed circuit board 20. Additional sealing is provided at rearward end 17 of the housing about cable 19.

The housing portions are preferably made of polystyrene or other easily molded rigid plastic material. Dome member 54 is preferably made of silicone rubber having a durometer in the range of 60–70, rendering it sufficiently flexible to perform the described functions for actuation and sealing, yet sufficiently hard to remain durable and positive acting. Contact disc 64 is preferably made of stainless steel, permanently attached to the silicone rubber, and has a thickness of 0.006±0.001 inch. Printed circuit board 20 is made of copper foil clad fiberglass wherein the circuit is produced through a photo-chemical etching process to remove copper foil in unwanted areas. A nickel plating is then applied to the remaining copper foil, and the remaining circuitry is then drilled to its final configuration.

The electrosurgical generator pencil described herein is reliable, safe and easily operable and can be fabricated simply and inexpensively. The sealing effected on opposite sides of flange 59 renders the switch simple to assemble without sacrificing sealing effectiveness. Reliable switch actuation is assured by providing a sharp annular edge on disc 64 so that the edge can cut through oxide film on the printed circuit board contacts when forced perpendicularly onto the contacts and when scraped along the contact surfaces as the disc is expanded in response to further actuation force.

While we have described and illustrated various specific embodiments of our invention, it will be clear that variations of the details of construction which are specifically illustrated and claimed may be resorted to without departing from the true spirit and scope of the invention as defined in the appended claims.

What is claimed is:

1. In an electrosurgical pencil of the type having an electrode blade energizable via an electrical signal, a switch structure for permitting selective application of said signal to said electrode blade, the improvement comprising:

an electrically insulative hollow housing from which said electrode blade projects and into which said electrical signal is delivered, said housing having at least one housing wall with an aperture defined therethrough to provide communication between outside and inside the housing;

circuit carrying means disposed inside said housing in substantially fixed spatial relation to said housing wall and including a circuit surface having first and second spaced electrical circuit contacts at least parts of which are disposed in substantial registration with said aperture;

a resilient dome-like member, disposed in said housing, tapering from an open first end having a relatively large peripheral dimension to a closed second end having a relatively small peripheral dimension, said dome-like member having an interior space, said closed second end being disposed in substantial registration with said aperture, said first end including a flange portion with a first sealing surface disposed substantially flush against said circuit surface entirely surrounding and forming a closed sealing path about said parts of said first and second contacts, said flange portion further including a second sealing surface facing in a direction opposite said first sealing surface, said dome-like member including a tapered peripherally continuous connecting wall extending between said first and second ends, said connecting wall being sufficiently flexible to permit said second end to be resiliently displaced axially at least a predetermined axial displacement toward said first end in response to an actuating force applied to said second end through said aperture;

electrically conductive means secured to said second end and disposed in said open interior space for electrically bridging said first and second contacts in response to said predetermined axial displacement of said second end; and structural means extending from said housing wall into flush contact with said second sealing surface to provide a first peripherally continuous sealing engagement with said second sealing surface outside said interior space while compressively urging said first sealing surface into engagement with said circuit surface.

2. The electrosurgical pencil according to claim 1 wherein said connecting wall is considerably thicker proximate said second end than proximate said flange.

3. The pencil according to claim 1 wherein said connecting wall includes a first length connected to said flange, a second length connected to said second end, said second length being substantially thicker than said first length, and a transition portion between said first and second lengths, said transition portion defining a flexure region in said connecting wall such that said connecting wall flexes in response to axial movement of said second end of said dome-like member toward said first end.

4. The electrosurgical pencil according to claim 3 wherein said resilient dome-like member further comprises an axial projection extending from said second end into said interior space, said axial projection having a distal end facing said circuit surface; and wherein said electrically conductive means comprises a metal member secured to said distal end of said axial projection.

5. The electrosurgical pencil according to claim 4 wherein said distal end is concave, and wherein said metal member is a concave disk-like member having a sharp peripheral edge positioned to contact said first and second contacts in response to said predetermined axial displacement of said second end, wherein said peripheral edge is sufficiently sharp to cut through oxidized film which may form on said first and second contacts.

6. The electrosurgical pencil according to claim 5 wherein said disk-like member has the same size and shape as said distal end and is outwardly expandable when compressed against said circuit surface by said axial projection.

7. The electrosurgical pencil according to claim 6 wherein said circuit carrying means has a vent hole defined therethrough for providing communication through said circuit carrying means to said interior space of said dome-like member.

8. The electrosurgical pencil according to claim 6 wherein said flange has an annular configuration, said connecting wall has a frusto-conical configuration, and said sharp peripheral edge has an annular configuration.

9. The electrosurgical pencil according to claim 1 wherein said resilient dome-like member further comprises an axial projection extending from said second end into said interior space, said axial projection having a distal end facing said circuit surface; and wherein said electrically conductive means comprises a metal member secured to said distal end of said axial projection.

10. The electrosurgical pencil according to claim 9 wherein said distal end is concave, and wherein said metal member is a concave disk-like member having a sharp peripheral edge positioned to contact said first and second contacts in response to said predetermined axial displacement of said second end, wherein said peripheral edge is sufficiently sharp to cut through oxidized film which may form on said first and second contacts.

11. The electrosurgical pencil according to claim 10 wherein said disk-like member has the same size and shape as said distal end and is outwardly expandable when compressed against said circuit surface by said axial projection.

12. The electrosurgical pencil according to claim 1 wherein said flange has an annular configuration and said connecting wall has a frusto-conical configuration.

13. In an electrosurgical pencil, a switch structure comprising:

an electrically insulative hollow housing having at least one housing wall with an aperture defined therethrough to provide communication between outside and inside the housing;

circuit carrying means disposed inside said housing in substantially fixed spatial relation to said housing wall and including a circuit surface having first and second spaced electrical circuit contacts at least parts of which are disposed in substantial registration with said aperture;

a resilient dome-like member, disposed in said housing, having an open first end, a closed second end, and a peripheral continuous connecting wall forming said first and second ends, said open first end being disposed in abutting relation with said circuit surface, said closed second end being disposed in substantial registration with said aperture, said second end being resiliently movable toward said first end in response to an actuating force applied to said second end through said aperture, said dome-like member including an axial projection extending from said second end toward said first end and having a distal end facing said circuit surface; wherein said first end includes a flange portion with a first sealing surface disposed substantially flush against said circuit surface entirely surrounding and forming a closed sealing path about said parts of said first and second contacts, said flange portion further including a second sealing surface facing in a direction opposite said sealing surface, and further comprising structural means extending from said housing wall into flush contact with said second sealing surface to provide a first peripherally continuous sealing engagement with said second sealing surface outside said dome-like member while urging said first sealing surface into engagement with said circuit surface; and electrically conductive means secured to said distal end of said axial projection in spaced relation from said circuit surface and movable to electrically bridge said first and second contacts in response to a predetermined axial displacement of said second end toward said second surface, wherein said electrically conductive means is a concave disk-like member having a sharp peripheral edge positioned to contact said first and second contacts in response to said predetermined axial displacement of said second end, wherein said peripheral edge is sufficiently sharp to cut through oxidized film which may form on said first and second contacts.

14. The electrosurgical pencil according to claim 13 wherein said disk-like member has the same size and shape as said distal end and is outwardly expandable when compressed against said circuit surface by said axial projection.

15. The electrosurgical pencil according to claim 13 wherein said connecting wall has a generally frusto-conical configuration which flexes to permit resilient axial movement of said second end toward said first end.

16. The pencil according to claim 15 wherein said connecting wall includes a first length connected to said flange, a second length connected to said second end, said second length being substantially thicker than said first length, and a transition portion between said first and second lengths, said transition portion defining a flexure region in said connecting wall such that said connecting wall flexes in response to axial movement of said second end of said dome-like member toward said first end.

* * * * *